United States Patent [19]
Paul et al.

[11] Patent Number: 6,013,164
[45] Date of Patent: Jan. 11, 2000

[54] ELECTOKINETIC HIGH PRESSURE HYDRAULIC SYSTEM

[75] Inventors: Phillip H. Paul, Livermore; David J. Rakestraw, Fremont, both of Calif.

[73] Assignee: Sandia Corporation, Livermore, Calif.

[21] Appl. No.: 08/882,725

[22] Filed: Jun. 25, 1997

[51] Int. Cl.[7] .................................................. B01D 61/44
[52] U.S. Cl. .................... 204/450; 204/600; 204/647; 204/648
[58] Field of Search .................. 204/450, 600, 204/647, 648

[56] References Cited

U.S. PATENT DOCUMENTS

| | | | |
|---|---|---|---|
| 3,923,426 | 12/1975 | Theeuwes | 417/48 |
| 4,886,514 | 12/1989 | Maget | 604/891.1 |
| 4,908,112 | 3/1990 | Salvatore | 204/299 |
| 5,441,613 | 8/1995 | McCormick et al. | 204/180.1 |
| 5,571,410 | 11/1996 | Swedberg et al. | 210/198.2 |
| 5,573,651 | 11/1996 | Dasgupta et al. | 204/601 |
| 5,593,838 | 1/1997 | Zanzucchi et al. | 204/450 |

OTHER PUBLICATIONS

Liu, Shaorong and Purnendu K. Dasgupta. Analytica Chimica Acta, 283, 739–745. 1993. Electroosmotically pumped capillary flow–injection analysis.

Dasgupta, Purnendu and Shaorong Liu. Analytical Chemistry, 66, 1792–1798. 1994. Electroosmosis: A reliable fluid propulsion system for flow injection analysis.

Liu, Shaorong and P.K. Dasgupta. Analytica Chimica Acta, 268, 1–6. 1992. Flow injection analysis in the capillary format using electroosmotic pumping.

Rastog, R.P., Journal of Scientific and Industrial Research, 28, 298–292. 1969. Irreversible Thermodynamics of Electro–osmotic Effects.

Cooke, Claude E. Jr. Journal of Chemical Physics, 23, 2299–2303. 1995. Study of electrokinetic effects using sinusoidal pressure and voltage.

Pretorius, Victor; Hopkins, B.J. and J.D. Schieke. Journal of Chromatography, 99, 23–30. 1974. A new concept for high speed liquid chromatography.

*Primary Examiner*—Arun S. Phasge
*Attorney, Agent, or Firm*—Donald A. Nissen

[57] ABSTRACT

A compact high pressure hydraulic system having no moving parts for converting electric potential to hydraulic force and for manipulating fluids. Electro-osmotic flow is used to provide a valve and means to compress a fluid or gas in a capillary-based system. By electro-osmotically moving an electrolyte between a first position opening communication between a fluid inlet and outlet and a second position closing communication between the fluid inlet and outlet the system can be configured as a valve. The system can also be used to generate forces as large as 2500 psi that can be used to compress a fluid, either a liquid or a gas.

22 Claims, 2 Drawing Sheets

ELECTOKINETIC HIGH PRESSURE HYDRAULIC SYSTEM

STATEMENT OF GOVERNMENT INTEREST

This invention was made with Government support under contract no. DE-AC04-94AL85000 awarded by the U. S. Department of Energy to Sandia Corporation. The Government has certain rights in the invention.

CROSS-REFERENCE TO RELATED APPLICATIONS

Not Applicable

BACKGROUND OF THE INVENTION

This invention pertains generally to a method for producing high pressures that requires no moving mechanical parts and particularly to the use of electro-osmotic flow to produce a high pressure system for compressing and manipulating fluids in packed microchannels, in general, and capillaries, in particular.

The phenomenon of electro-osmosis, in which the application of an electric potential to an electrolyte in contact with a dielectric surface produces a net force on a fluid and thus a net flow of fluid, has been known since Reuss in 1809. The physics and mathematics defining it and its associated phenomenon streaming potential, both part of a larger class of electrochemical phenomena, namely electrokinetic effects, have been extensively explored, *Introduction to Electrochemistry*, S. Glasstone, 1942, pp. 521–529 and R. P. Rastogi, "Irreversible Thermodynamics of Electro-osmotic Flow", *J. Sci. and Industrial Res.*, 28, 284, 1969. In like manner, electrophoresis, the movement of charged particles through a stationary medium under the influence of an electric field, has been extensively studied and employed in the separation and purification arts.

The use of electro-osmotic flow has been wide spread and has found wide ranging applications in chemical analysis. The use of electro-osmostic flow for fluid transport in packed bed capillary chromatography was first documented by Pretorius, et. al., "Electro-osmosis—A New Concept for High-Speed Liquid Chromatography", *J. Chromatography*, 99, 23–30, 1974. Although the possibility of using this phenomenon was recognized two decades ago, the effective use of this method has only recently been demonstrated and has just begun (within the last year) to provide commercial utility.

As set forth hereinabove, although electro-osmosis has been used extensively to move or pump fluids, except for measurements of the streaming potential, there appears to be no recognition that this same phenomenon can be used to generate large pressures, or resistive forces, (in excess of 2500 psi) which can be used to compress or pump fluids and manipulate fluid flow generally in capillary-based systems.

SUMMARY OF THE INVENTION

The present novel invention uses electro-osmotic flow to provide a high pressure hydraulic system, having no moving mechanical parts, for pumping and/or compressing fluids and manipulating fluid flow in packed (i.e., having a porous dielectric material disposed in a fluid passageway) capillary-based systems (microsystems).

The invention comprises at least one capillary channel or microchannel forming a fluid passageway and having a porous dielectric medium disposed therein between one or more spaced electrodes. The porous dielectric medium can comprise small particles, high surface area structures fabricated within the microchannel, or microporous materials. An electric potential can be applied between the electrodes in contact with an electrolyte (i.e., a solution containing ions and generally capable of ionic conduction) contained within the pores of the porous dielectric medium in order to cause the electrolyte to move in the microchannel. The present invention can be characterized by two separate embodiments.

In one embodiment, the invention is configured such that an electrolyte contained in a porous dielectric medium disposed within a capillary or microchannel can act as a valve; the electrolyte being selectively moveable between a first position opening communication between a fluid inlet and an outlet and a second position closing communication between the fluid inlet and outlet. Opening and closing the valve is provided by applying an electric potential between the spaced electrodes sufficient to cause the electrolyte to move from the first position to the second. The process can be reversed simply by reversing the polarity of the electric potential.

The inventors have further discovered that by applying an electric potential to an electrolyte contained in a porous dielectric disposed within a capillary or microchannel, the system disclosed herein is capable of exerting high pressures (e.g., at least 2500 psi). Thus, in a second embodiment, the invention is configured to compress a fluid, which can be either a liquid or a gas. Here a fluid outlet can be either completely sealed or constricted such that when an electric potential is applied between spaced electrodes, movement of the electrolyte causes the fluid which resides between the electrolyte and the sealed or constricted outlet to be compressed.

The above-described electrokinetic high pressure hydraulic system has several advantageous features. There are no moving mechanical parts and all liquid seals, thus the system is not subject to frictional wear. Since the system is driven electrically and has no moving mechanical parts it can be rapidly turned on and off. By applying periodic electrical potentials, whose periods can be various functions of time, to a plurality of spaced electrodes different timing arrangements such as might be useful for varying compression and valving cycles can be effected. Moreover, the system is capable of remote operation.

BRIEF DESCRIPTION OF THE DRAWINGS

The accompanying drawings, which are incorporated in and form part of the specification, illustrate the present invention and, together with the description, explain the invention. In the drawings like elements are referred to by like numbers.

FIG. 1(a) shows the valve in the open position.

FIG. 1(b) shows the valve in the closed position.

DETAILED DESCRIPTION OF THE INVENTION

Figure 1A:
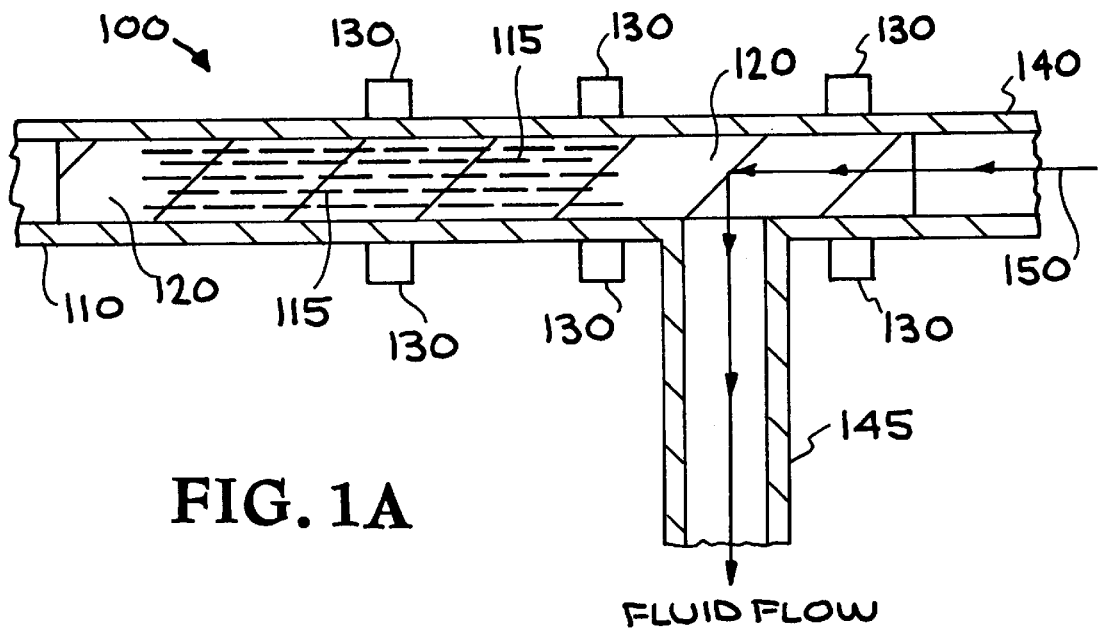
FIGS. 1a and 1b illustrates a valve embodiment of the present invention.

The present invention pertains generally to a high pressure hydraulic system and is particularly adapted for use in packed capillary-based systems. Electro-osmotic flow is used to provide a high pressure hydraulic system having no moving mechanical parts for pumping and/or compressing fluids and manipulating fluid flow within capillaries.

For the purpose of describing the invention disclosed herein the term microchannel, as used hereinafter, will refer to a flow channel whose internal dimensions are on the order of tens to hundreds of microns. Generally, these systems are referred to as capillary or capillary-based systems, however, the flow channels contemplated by this invention can have an arbitrary cross-sectional geometry, in addition to the circular cross-section conventionally associated with capillaries, and can be fabricated from any material providing that the material is not an electrical conductor.

It is contemplated that the present invention can be advantageously used in Microsystems (i.e., systems having dimensions on the order of tens to hundreds of microns) for fluid manipulation generally and, in particular, for compression/expansion of gases and high pressure injection of fluids. The present invention can also find advantageous use as a miniature vacuum pump or a miniature hydraulic pump. Moreover, because the present system exhibits only a very small dead volume it can be used for precise handling of gases.

In order for the electro-osmotic forces useful for this invention to be generated it is necessary that a porous dielectric medium be present in at least one of the microchannels. It is known in the art that electro-osmosis is generally attributable to the formation of an electric double layer at the interface between a solid and a liquid containing ions. As a consequence of the formation of the electric double layer, a electrically charged diffuse layer is formed extending from the solid-liquid interface into the bulk of the liquid. While a double layer can be formed anytime a liquid containing ionic species comes into contact with a solid surface, its physical manifestation is most easily observed in capillary systems. Here, under the influence of a tangential electric field the diffuse layer is caused to move and will flow at a constant rate depending upon the equilibrium established between frictional forces developed between the moving liquid and the wall of the capillary and the electro-osmotic force due to the electric forces acting on the excess ionic charge in the diffuse layer. If the liquid, under the influence of electro-osmotic forces, is allowed to accumulate at the outlet end of the capillary an excess hydrostatic pressure can be developed which can eventually counter-balance the electro-osmotic forces.

Porous dielectric materials useful for this invention can take a number of forms in addition to the more conventional silica structures such as beads or frits. Such structures can be fabricated, by way of example, by lithographic patterning and etching, direct injection molding, sol-gel processes, and high energy lithography combined with electroforming and molding (LIGA) as well as organic polymeric materials.

A valve embodiment of the present invention can be illustrated by reference to FIG. 1(a). Valve 100 comprises a T-shape flow system, wherein microchannel 110 contains a porous dielectric 120, extending past outlet 145 about 1–2 channel diameters, that can include fine particles, preferably silica having a diameter of about 100 nm to 5 µm, or other high surface area features such as might be produced by microfabrication methods known to those skilled in the art, preferably by lithographic etching, and which present a porous matrix having a high surface area for electrolyte solution 115 to flow through. Fluid inlet 140 and outlet 145 in communication with microchannel 110 provide for the flow of a fluid (liquid or gas) 150 therethrough.

Figure 1B:
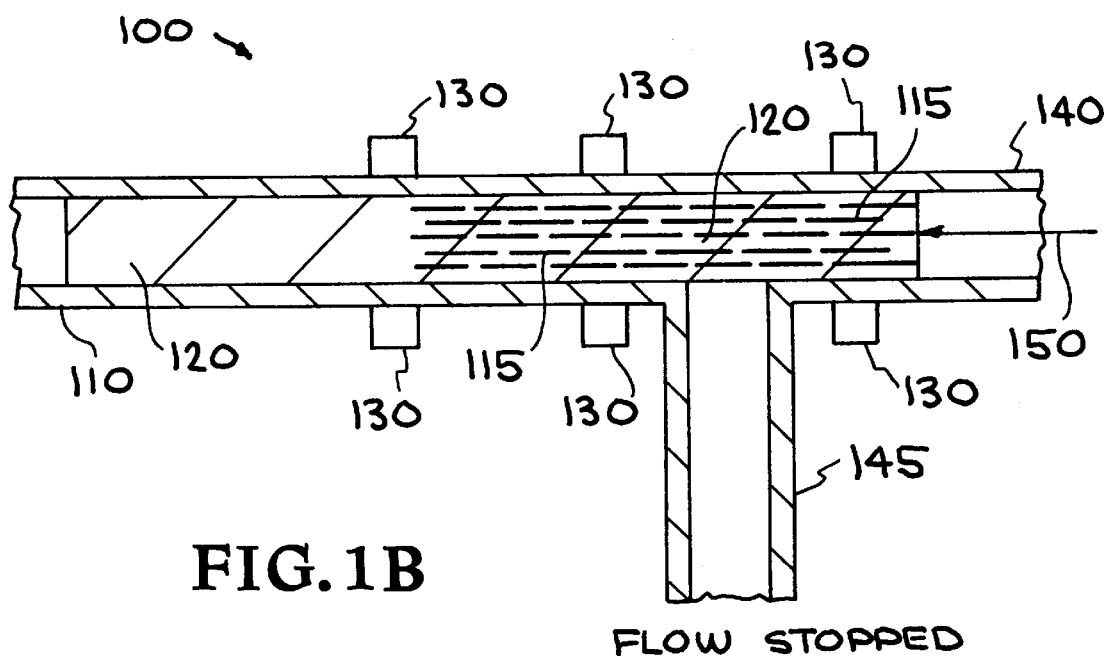

Referring now to FIG. 1(b), in order to close communication between fluid inlet 140 and outlet 145 an electric potential is applied by a power supply (not shown) to spaced electrodes 130 to provide the electro-osmotic force required to move electrolyte 115, to close fluid outlet 145, and prevent fluid 150 from flowing through outlet 145. Valve 100 can be opened by simply shutting off the electric potential applied to spaced electrodes 130. Valve 100 can be caused to operate in the opposite direction by simply reversing the sign of the electric potential applied to spaced electrodes 130.

It is contemplated that the electric potential applied between spaced electrodes 130 can, in addition to the step function form described hereinabove, assume various other forms suitable to the operation of the system described herein such as oscillatory having a varying shape and period.

Figure 2:
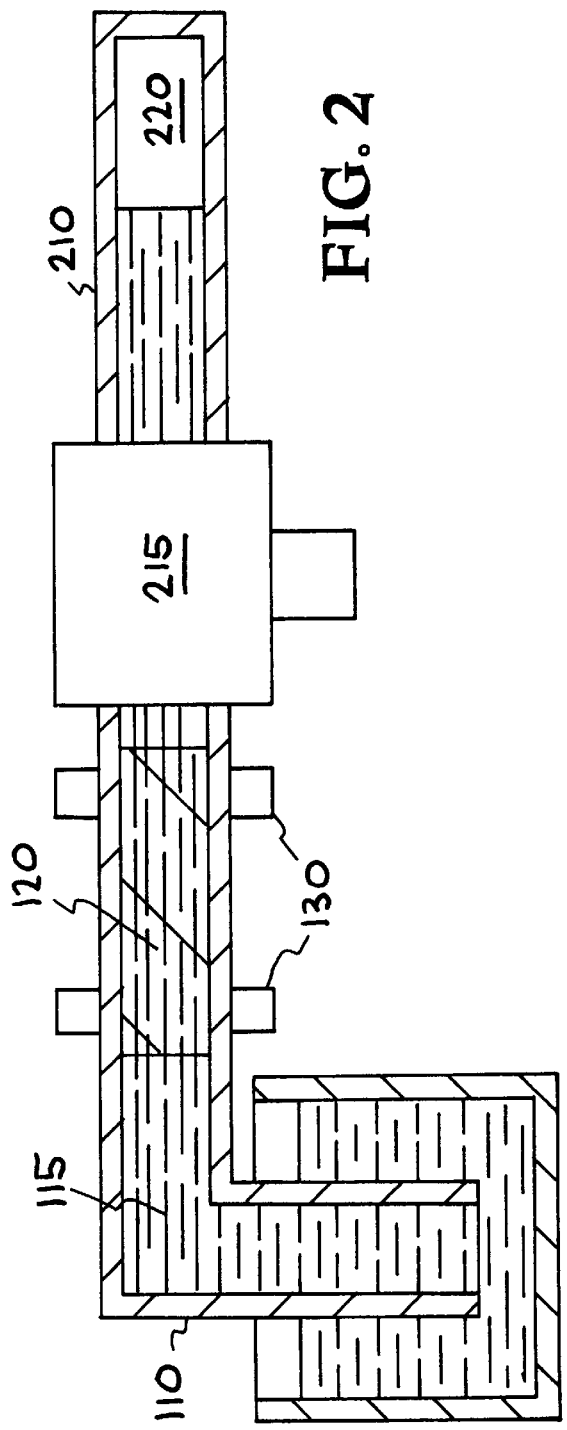
FIG. 2 illustrates a compressor embodiment.

The use of the present invention as a means for compressing a fluid, preferably a gas, within a flow channel can be illustrated by reference to FIG. 2. One open end of microchannel 110 containing porous dielectric material 120 is submerged in electrolyte 115. The opposite open end of microchannel 110 is connected one leg of "T" fitting 215. One end of capillary 210 is connected to the opposite leg of fitting 215 and the other end of capillary 210 can be sealed shut. An electric potential is applied by a power supply (not shown) between spaced electrodes 130 in contact with electrolyte 115. Electro-osmotic forces generated in microchannel 110 cause electrolyte 115 to advance by electro-osmotic pumping into microchannel 110 and further into capillary 210. The advance of electrolyte 115 (pumping) is stopped when the pressure of fluid 220 constrained in the sealed end of capillary 210 is high enough to counterbalance the electro-osmotic force produced by the electric potential applied to spaced electrodes 130, i.e., when the pressure of fluid 220 equals the electro-osmotic force generated by the applied electric potential. Shutting off or reducing the applied electric potential causes electrolyte 115 to retreat until the forces are once again balanced.

Figure 3:
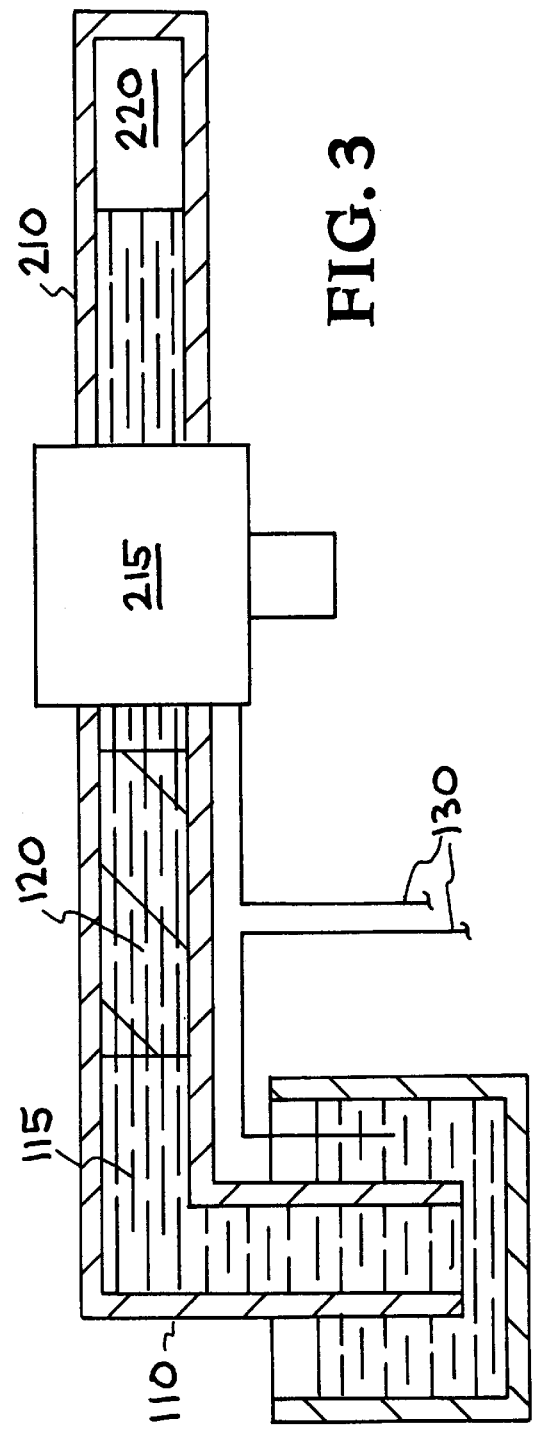
FIG. 3 shows an application of the present invention to compressing a gas.

By way of example, a 15 cm long fused silica capillary 110 (as shown in FIG. 3) having a 75 µm inside diameter was packed with silica spheres 120 having a diameter of about 3 µm. The packed column was wetted with electrolyte 115, here water buffered with a trisodium phosphate buffer to a pH of 8.6. One end of the packed capillary 110 was then submerged in electrolyte 115 that also contained one electrode 130. The opposite end of packed capillary 110 was sealed into one leg of HPLC fitting 215 that served as another electrode 130. One end of an open fused silica capillary 210 was sealed into the other leg of HPLC fitting 215. Power was supplied to electrodes 130 to cause electrolyte 115 to be electro-osmotically pumped through packed column 110 and into open capillary 210. Having wetted a portion of the open capillary the opposite end of open capillary 210 was sealed shut. Power was again supplied to electrodes 130 until sufficient pressure was reached to counterbalance the electro-osmotic pumping force. For an applied field of about 300 V/cm a pressure in excess of 2500 psi was observed in the sealed end of capillary 210.

The pressure generated in this system is proportional to the electric potential and scales linearly with the length of the capillary, limited only by power dissipation or dielectric breakdown. In this context, it should be noted that in the presence of an applied field there will be ohmic heating of the microchannel and its contents and that this ohmic heating will have a substantially radial profile. The combination of a relatively high thermal conductivity aqueous electrolyte and the small physical dimensions involved suggest that there will be only a small radial temperature gradient as a result of this heating. It is straight forward to efficiently remove the heat generated in a microchannel, which can be a fused capillary, using forced air or immersion in a heat transfer liquid.

In summary, the present novel invention is useful generally in any application where manipulation of fluids in microchannels, in general, and capillary channels, in particular, is required, particularly in such applications as remote actuation of valves and other components or where a compressed fluid can be used to drive a fluid charge at high pressure on demand through the action of a valve.

It will be understood that the above described arrangements of apparatus and the methods therefrom are merely illustrative of applications of the principles of this invention and many other embodiments and modifications may be made without departing from the spirit and scope of the invention as defined in the claims.

SEQUENCE LISTING

Not Applicable.

We claim:

1. A valve for the manipulation of a fluid, comprising:
   a) a microchannel having an inlet and an outlet and a porous dielectric material disposed therebetween;
   b) at least one fluid inlet and fluid outlet in communication with the outlet of said microchannel;
   c) an electrolyte contained within the porous dielectric material said electrolyte being selectively moveable between a first position opening communication between the fluid inlet and the fluid outlet and a second position closing communication between the fluid inlet and the fluid outlet; and
   d) spaced electrodes for moving said electrolyte between the first and second positions.

2. The valve of claim 1, wherein said microchannel has a circular cross-section.

3. The valve of claim 1, wherein said microchannel comprises a fused silica capillary.

4. The valve of claim 1, wherein the porous dielectric material includes silica particles.

5. The valve of claim 4, wherein the silica particles have a diameter of between about 100 nm and 5 $\mu$m.

6. The valve of claim 1, wherein the porous dielectric material includes porous dielectric materials fabricated by processes selected from the group consisting of lithographic patterning and etching, direct injection molding, sol-gel processing, and electroforming.

7. The valve of claim 1, wherein the porous dielectric material includes organic polymer materials.

8. The valve of claim 1, wherein the fluid is a gas.

9. A method for manipulating a flow of a fluid, comprising:
   applying an electric potential to spaced electrodes in communication with an electrolyte contained within a porous dielectric disposed within a microchannel, thereby causing the electrolyte to move from a first position, wherein a fluid inlet and a fluid outlet are in open communication, to a second position closing communication between the fluid inlet and outlet; and
   shutting off the electric potential, thereby causing the electrolyte to move to the first position.

10. The method of claim 9, wherein the fluid is a gas.

11. The method claim 9, wherein said step of applying includes applying an electric potential that varies in time.

12. A system for compressing a fluid, comprising:
   a) a microchannel having an inlet and an outlet and a porous dielectric material disposed therebetween;
   b) an electrolyte contained within said microchannel;
   c) spaced electrodes in communication with said electrolyte; and
   d) at least one flow channel in communication with the outlet of said microchannel, wherein said flow channel contains a fluid and is provided with at least one fluid inlet and one fluid outlet configured such that when an electro-osmotic force is applied to said electrolyte the fluid is compressed.

13. The system of claim 12, wherein said microchannel has a circular cross-section.

14. The system of claim 12, wherein said microchannel and flow channel each comprise a fused silica capillary.

15. The system of claim 12, wherein the porous dielectric material includes silica particles.

16. The system of claim 15, wherein the silica particles have a diameter of between about 100 nm and 5 $\mu$m.

17. The system of claim 12, wherein the porous dielectric material includes porous dielectric materials fabricated by processes selected from the group consisting of lithographic patterning and etching, direct injection molding, sol-gel processing, and electroforming.

18. The system of claim 12, wherein the porous dielectric includes organic polymer materials.

19. A method for compressing a liquid or a gas, comprising:
   applying an electric potential to spaced electrodes in communication with an electrolyte contained within a porous dielectric disposed within a microchannel having one end sealed, thereby to cause the electrolyte to move compressing a fluid contained between the electrolyte and the sealed end; and
   shutting of the electric potential to release the pressure on the fluid.

20. The method of claim 19, wherein the step of shutting includes reversing the electric potential.

21. An apparatus for the manipulation of a fluid, consisting of:
   a) a flow channel for passage of a fluid having an inlet and an outlet, wherein the inlet and outlet ends are disposed at an angle to each other; and
   b) means for generating an electro-osmotic force in communication with the inlet end of said flow channel.

22. An apparatus for compressing a fluid, consisting of:
   a) a flow channel for passage of a fluid having an inlet and an outlet, wherein the outlet end of said channel is constricted; and
   b) means for generating an electro-osmotic force in communication with the inlet end of said flow channel.

* * * * *